United States Patent
Herrmann et al.

(10) Patent No.: US 7,878,709 B2
(45) Date of Patent: Feb. 1, 2011

(54) RETAINING APPARATUS FOR RETAINING A FLEXIBLE CONNECTING ELEMENT ON A DEVICE

(75) Inventors: Norbert Herrmann, Ebnath (DE); Jochen Miguel Löseken, Bayreuth (DE)

(73) Assignee: Siemens Aktiengesellschaft, München (DE)

( * ) Notice: Subject to any disclaimer, the term of this patent is extended or adjusted under 35 U.S.C. 154(b) by 191 days.

(21) Appl. No.: 12/297,149

(22) PCT Filed: Feb. 26, 2007

(86) PCT No.: PCT/EP2007/051806

§ 371 (c)(1),
(2), (4) Date: Oct. 14, 2008

(87) PCT Pub. No.: WO2007/122029

PCT Pub. Date: Nov. 1, 2007

(65) Prior Publication Data

US 2010/0150317 A1    Jun. 17, 2010

(30) Foreign Application Priority Data

Apr. 18, 2006  (DE) .................. 10 2006 017 843

(51) Int. Cl.
  *H05G 1/06* (2006.01)
(52) U.S. Cl. .................................... 378/194
(58) Field of Classification Search ............. 378/101, 378/193–198
  See application file for complete search history.

(56) References Cited

U.S. PATENT DOCUMENTS

| 2,122,988 A | * | 7/1938 | Nelson | 378/194 |
| 6,065,705 A | | 5/2000 | Schmitt | 242/375.1 |

FOREIGN PATENT DOCUMENTS

| DE | 16372 | 2/1959 |
| DE | 296 09 895 U1 | 1/1997 |
| DE | 19747393 C2 | 11/1999 |
| FR | 77590 | 3/1962 |
| FR | 1 360 575 | 5/1964 |

OTHER PUBLICATIONS

German Office Action dated Mar. 23, 2007 with English translation.
International Search Report dated Jul. 17, 2007 with English translation.
Written Opinion dated Jul. 17, 2007 with English translation.

* cited by examiner

*Primary Examiner*—Courtney Thomas
(74) *Attorney, Agent, or Firm*—Brinks Hofer Gilson & Lione

(57) ABSTRACT

A retaining apparatus having a fastening element for fastening to a device, a first retaining element which is arranged on the fastening element in such a manner that it can be pivoted about a first axis, and a second retaining element which is arranged in such a manner that it can be pivoted about a second axis that is oriented perpendicular to the first axis and is designed to retain a flexible connecting element such that it can be moved forwards and backwards ensures a definable profile of the connecting element with little mechanical loading. A medical device, in particular in the form of a C-arc X-ray device, is provided with this retaining apparatus in a particularly advantageous manner.

14 Claims, 2 Drawing Sheets

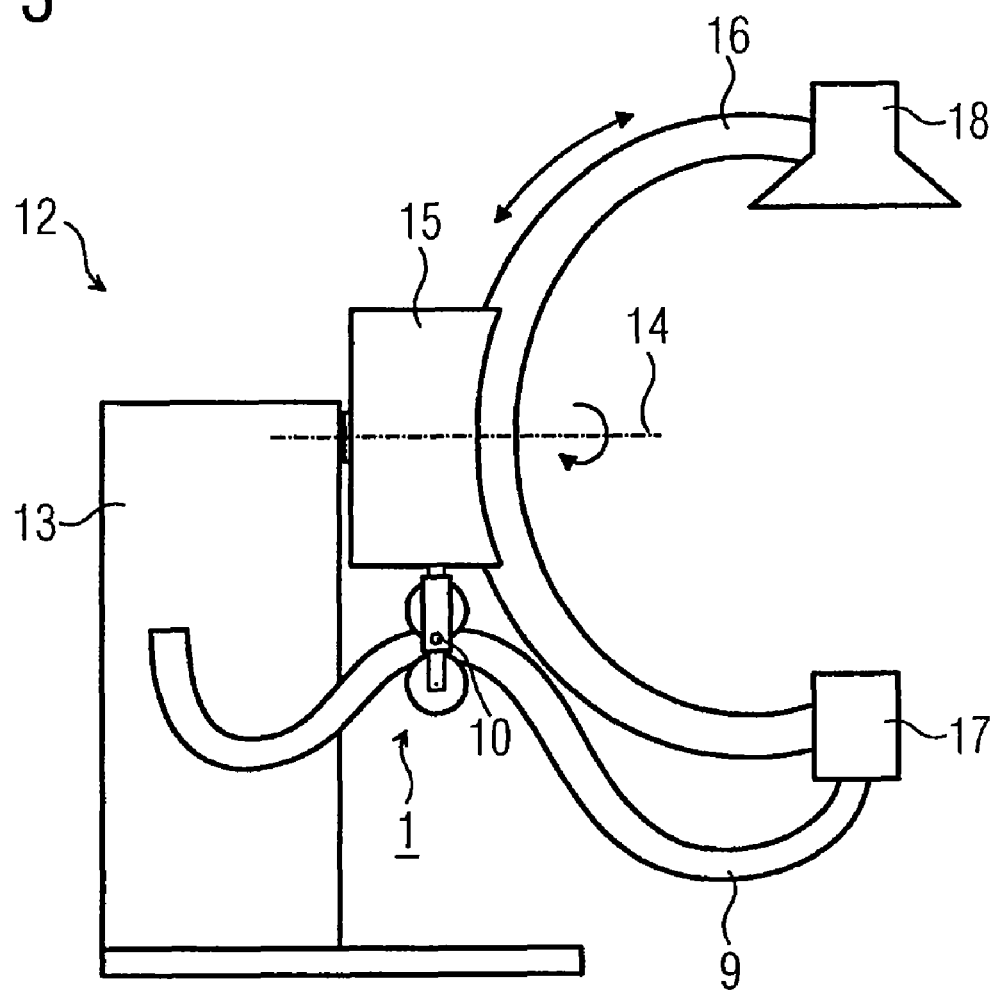

RETAINING APPARATUS FOR RETAINING A FLEXIBLE CONNECTING ELEMENT ON A DEVICE

The present patent document is a §371 nationalization of PCT Application Serial Number PCT/EP2007/051806, filed Feb. 26, 2007, designating the United States, which is hereby incorporated by reference. This patent document also claims the benefit of DE 10 2006 017 843.2, filed Apr. 18, 2006, which is also incorporated by reference.

BACKGROUND

The present embodiments relate to a mounting apparatus for mounting a flexible connecting element on a device.

A flexible connecting element, such as a cable hose, may be disposed on a device. The flexible connecting element connects two parts of the device that are movable relative to one another. For example, a medical C-arch X-ray system has a C-arm that is movable relative to a stationary part of the device and has an X-ray emitter and an X-ray receiver. For operation, the X-ray emitter is supplied with electrical high voltage, which is transmitted from the stationary part to the X-ray emitter by a flexible connecting element, in the form of a cable hose. A high-voltage cable disposed in the cable hose is used for transmitting electrical current. The high-voltage cable has a limited maximum length, so that rigidly mounting the cable hose near the device is disadvantageous because of an overly long connection distance that results from this mounting. The cable hose is exposed to as little mechanical tensile or flexing stress as possible from the relative motion of the C-arm with respect to the stationary part.

The cable hose is secured on one side only at one point of the stationary part of the C-arch X-ray system and on the other side at one point of the C-arm, with the cable hose hanging free between these two points. Because of the unsupported free course of the cable hose between the two aforementioned points, the cable hose is exposed, by its own weight, to comparatively high tensile stress. The cable hose is poorly controlled in its course because of the suspension from only two points. Because of gravity, depending on the relative position of the C-arm with respect to the stationary part, the cable hose sags to a varying extent and thus limits the freedom of motion in the vicinity of the C-arch X-ray system.

German Patent DE 197 47 393 C2 discloses a weight-compensating device with a cable drum for receiving a load-bearing cable. The cable drum is stressed by the force of a spiral spring element. The load-bearing cable can be used to bear a useful load. In FIG. 1 of this reference, a hoselike connecting element is embodied between a ceiling tripod on the one hand and an X-ray emitter on the other.

SUMMARY AND DESCRIPTION

The present embodiment may obviate one or more of the drawbacks or limitations inherent in the related art. For example, in one embodiment, a flexible connecting element may be mounted on a device in such a way that despite the least possible mechanical stress on the flexible connecting element, a definable course of the connecting element is assured.

Because of the pivotability of the first mounting element relative to the securing element about a first axis and the pivotability of the second mounting element relative to the first mounting element about a second axis oriented at right angles to the first axis, the connecting element is flexibly movable and has reduced mechanical stress. The mounting direction of the flexible connecting element in the mounting device is flexibly adjustable, because of the two axes oriented at right angles to one another. Because of the biaxial pivotability, the connecting element may yield to rotary forces in a way that makes for low wear. The connecting element is mounted such that it is movable back and forth in a guided way. A movable guidance of the course is assured despite a course of the connecting element that is definable by the applicable securing of the mounting apparatus to the device. Because of the movability back and forth, the connecting element may yield to tensile forces in a way that involves little mechanical stress.

The mounting of the flexible connecting element is possible by an at least two-sided positive engagement of the flexible connecting element in the second mounting element.

Because the at least two-sided positive-engagement mounting is assured by at least two rollers of the second mounting element, which are embodied for guiding the connecting element by contacting it on at least two sides, the flexible connecting element has little friction in the second mounting element and is movable back and forth with little mechanical stress.

A secure hold of the connecting element is possible by the second mounting element for mounting the connecting element that is a hose. A hose with a circular cross section enables rotation of the hose about its longitudinal axis in the second mounting element. The at least two rollers may have a concave roller profile that is adapted to the circular cross section of the hose. Accordingly, an especially secure positive-engagement hold of the hose in the second connecting element is assured. The adapted roller profile, despite the possible presence of contact pressure of the rollers against the hose, may provide a uniform mechanical stress on the hose, which is accordingly associated with only little wear.

The first mounting element may be a mounting fork. By a disposition of the second mounting element on the forklike end of the mounting fork, an especially secure hold of the second mounting element is possible despite a pivotability of the second mounting element about the second axis. The securing element is disposed on the tapered end of the mounting fork.

The mounting of the connecting element in the second mounting element by at least two-sided positive engagement is assured in that this second mounting element is a mounting frame that surrounds the connecting element. For example, the mounting frame may be essentially rectangularly, and on two opposed sides of the mounting frame, two rollers contacting the hose on both sides are disposed, while on the two remaining opposed sides of the second mounting element, a rotary hinge for securing purposes is disposed on the mounting fork, in each case centrally.

A mounting apparatus with the first axis at right angles to the respective securing surface on the device makes it possible in a simple way to transpose the connecting element parallel to the securing surface. This orientation of the first axis is made possible by a suitable fastening to the device.

In one embodiment, the first axis and/or the second axis extends through the center of the cross section of the connecting element. Accordingly, the lever forces occurring upon pivoting and thus the mechanical stress on the connecting element are reduced. By a course of the first and second axes through the center of the cross section of the connecting element, the connecting element, with the center of its cross section, is mounted inside the mounting apparatus at the same defined point, regardless of the pivoting orientation at the time. This makes an especially precisely definable course of the flexible connecting element possible, regardless of the pivoting orientation at the time.

By limiting the pivot angle range about the first axis and/or about the second axis in a predefined way, it is possible to define the course of the connecting element more exactly.

In one embodiment, a medical system may include a mounting apparatus in accordance with one of the embodiments described herein. Medical systems require an especially high degree of operating safety, so that it is advantageous to use a mounting apparatus which assures little mechanical stress and thus low wear of the flexible connecting element. Because of the exactly definable course of the connecting element, a compact structure while simultaneously assuring a high degree of freedom of motion for persons in the surrounding of the system is possible.

In one embodiment, the medical system may include a C-arch X-ray system, which may include an x-ray source (emitter) and x-ray detector. The need for a definable course of the connecting element with simultaneously low mechanical stress is especially great, because of the C-arm of the C-arch X-ray system that is movable over a wide range of motion relative to a stationary part of the system. The connecting element may be a cable hose for receiving a high-voltage line that is provided for supplying energy to an X-ray tube disposed on the C-arm.

In one embodiment, the mounting apparatus is secured by a securing element to a part of the C-arch X-ray system that is movable relative to a stationary part. The disposition of the mounting apparatus on this movable part is useful for the sake of flexible, wear-free mounting of the connecting element. The connecting element may be mounted by the mounting apparatus on the movable part in the form of a connecting part on which a C-arm of the C-arch X-ray system is movably supported. This connecting part is pivotable, for example, about a horizontal axis relative to the stationary part, and the C-arm is pivotable in rail-like fashion, guided by the connecting part, about a given patient who is to be examined.

In one embodiment, the mounting apparatus is operable to mount a hose with a high-voltage line leading from the stationary part of the C-arch system to an X-ray emitter on the C-arm. Since high-voltage lines have a limited maximum length, a course of the high-voltage line that is defined by the mounting apparatus and as a result can be made especially short is particularly advantageous.

BRIEF DESCRIPTION OF THE DRAWINGS

FIG. 3 illustrates a C-arch X-ray system with a connecting element.

DETAILED DESCRIPTION

Figure 1:
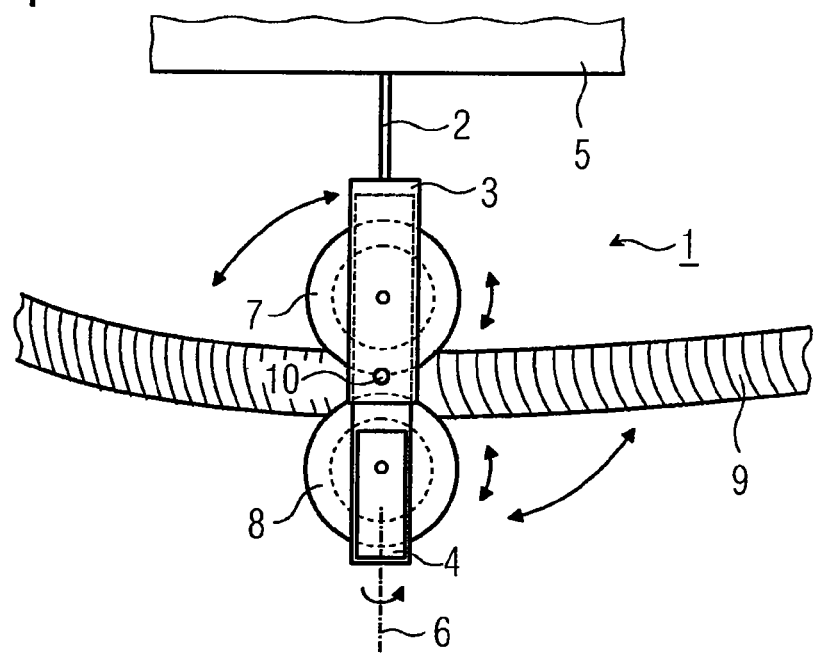
FIG. 1 illustrates one embodiment of a mounting apparatus.

FIG. 1 illustrates a side view of a mounting apparatus 1. The mounting apparatus includes a securing element 2, a first mounting element 3, and a second mounting element 4. The mounting apparatus 1 is secured by the securing element 2 to a device 5. The mounting element 4 is pivotable about a first axis 6 that is oriented perpendicular to the securing surface of the device 5. The second mounting element 4 is pivotable relative to the first mounting element 3 about a second axis at right angles to the first axis 6 and at right angles to the plane of the drawing. The second mounting element 4 includes two rollers 7, 8, which rest on two sides on a flexible connecting element in the form of a hose 9. The hose 9 is movable back and forth in the second mounting apparatus 4, guided by the rollers 7, 8. The two rollers 7, 8 are rotatably supported, so that the hose 9 is movable with little mechanical stress.

The two pivot axes 6 extend through the center point of the cross section of the hose 9, so that regardless of the pivoting about the two axes 6, the hose 9 extends at all times through the pivot point 10 defined by the mounting apparatus 1. The pivoting range about the two axes 6 is limited, in such a way that the hose 9 does not touch the device 5 in any pivoting setting.

Figure 2:
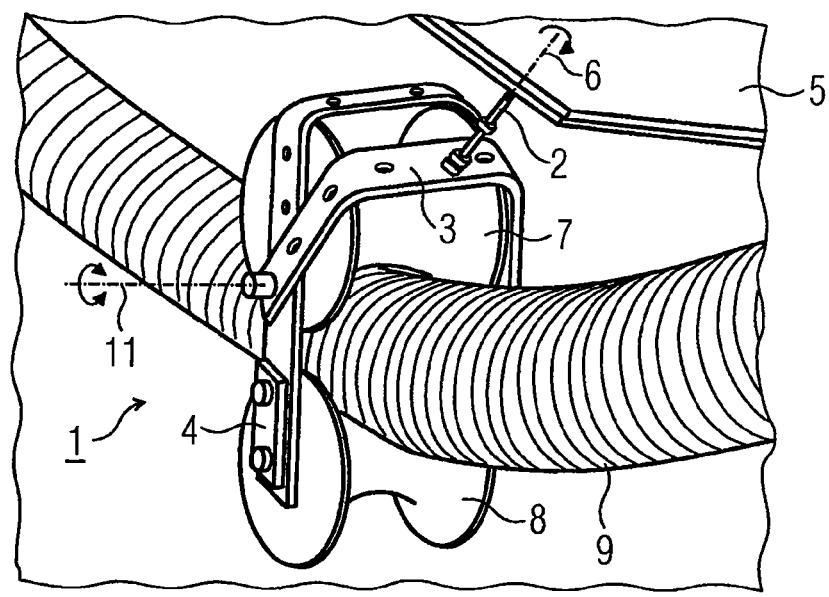
FIG. 2 illustrates the mounting apparatus of FIG. 1 in a modified pivoting setting.

FIG. 2 shows the mounting apparatus 1 of FIG. 1. The first mounting element 3 is pivoted relative to the securing element 2 about the first axis 6. The second mounting element 4 is pivoted relative to the first mounting element 3 about the axis 11. The first mounting element 3 is a mounting fork, on whose ends the second mounting element 4 is supported pivotably by hinges. The second mounting element 4 is a mounting frame. The hose 9 has a circular cross section. The rollers 6, 8 have a concave shape adapted to this circular cross section and assure a secure, low-wear hold of the hose 9.

Alternatively, a hose of rectangular cross section would also be conceivable, which is guided by a second mounting element with four rollers, offset from one another by 90° and contacting the hose on all four sides. Accordingly, a rectilinear roller profile may be appropriate.

FIG. 3 shows a C-arch X-ray system 12 with a stationary part 13, an intermediate part 15 rotatable relative to it about a horizontal axis 14, and a C-arm 16 pivotable relative to the intermediate part 15 by a rail-like guide and the C-arm has an X-ray emitter 17 and an X-ray detector 18. The X-ray emitter 17 and the X-ray detector 18 are each disposed on the opposite ends of the C-arm 16, for examination of a patient. The patient can be placed between them, by means of X-radiation.

The X-ray emitter 17 is connected to the stationary part 13 by a connecting element, in the form of a cable hose 9. A high-voltage line that supplies the X-ray emitter 17 with a high voltage furnished by the stationary part 13 is disposed in the cable hose 9. Between the rigid connections of the hose 9 to the stationary part 13 and the X-ray emitter 17, the hose 9 is retained by the mounting apparatus 1 that is secured to the intermediate part 15. The mounting apparatus 1 assures that the hose 9 extends through the pivot point 10. The hose 9 is pivotable about this pivot point 10 about the two axes 6, 11, as a function of the relative position at the time of the C-arm 16 and the stationary part 13. This intermediate mounting of the hose 9 by the mounting apparatus 1, despite a compact construction, assures an especially short, flexible course of the cable hose 9 while avoiding collisions of the hose 9 with the C-arch X-ray system 12.

As an alternative to supplying power, the hose 9 may be a gas or liquid line for supplying a gas or a liquid.

In one embodiment, a mounting apparatus with a securing element for securing to a device is provided. A first mounting element is disposed on the securing element pivotably about a first axis. A second mounting element is disposed pivotably about a second axis oriented at right angles to the first axis. The second mounting element may be used for mounting a flexible connecting element such that the connecting element can be moved back and forth. Accordingly, a definable course of the connecting element with little mechanical stress is assured. A medical system, for example, a C-arch X-ray system, is equipped with the mounting apparatus.

The invention claimed is:

1. A mounting apparatus for mounting a flexible connecting element on a device, the mounting apparatus comprising:
   a securing element for securing to the device;
   a first mounting element disposed on the securing element pivotably about a first axis; and
   a second mounting element that is disposed pivotably about a second axis oriented at a right angle to the first axis, the flexible connecting element being mounted on the second mounting element such that the connecting element is movably guided back and forth,
   wherein the first mounting element is a mounting fork comprising fork ends, the second mounting element being pivotably supported by the fork ends of the mounting fork.

2. The mounting apparatus as defined by claim 1, wherein the mounting of the flexible connecting element is provided by an at least two-sided positive engagement in the second mounting element.

3. The mounting apparatus as defined by claim 2, wherein the second mounting element includes at least two rollers, which guide the connecting element and contact the connecting element on at least two sides.

4. The mounting apparatus as defined by claim 3, wherein the connecting element is a hose having an at least approximately circular cross section.

5. The mounting apparatus as defined by claim 4, wherein the at least two rollers have a concave roller profile adapted to the circular cross section of the hose.

6. The mounting apparatus as defined by claim 1, wherein the second mounting element is a mounting frame that surrounds the connecting element.

7. The mounting apparatus as defined by claim 1, wherein the first axis is disposed at a right angle to a securing surface on the device.

8. The mounting apparatus as defined by claim 1, wherein the first axis and/or the second axis extend through the center of the cross section of the connecting element.

9. The mounting apparatus as defined by claim 1, wherein a pivot angle range about the first axis and/or about the second axis is predefined.

10. A medical system comprising:
    a C-arch X-ray system; and
    a mounting apparatus comprising:
       a securing element for securing to the C-arch X-ray system;
       a first mounting element disposed on the securing element pivotably about a first axis; and
       a second mounting element that is disposed pivotably about a second axis oriented at a right angle to the first axis, a flexible connecting element being mounted on the second mounting element such that the flexible connecting element is movably guided back and forth,
    wherein the first mounting element is a mounting fork comprising fork ends, the second mounting element being pivotably supported by the fork ends of the mounting fork.

11. The medical system as defined by claim 10, wherein the C-arch X-ray system includes an x-ray source and an x-ray detector.

12. The medical system as defined by claim 10, wherein the securing element is secured to a movable part of the C-arch X-ray system, the movable part being movable relative to a stationary part.

13. The medical system as defined by claim 12, wherein the movable part is an intermediate part, on which a C-arm of the C-arch X-ray system is movably supported.

14. The medical system as defined by claim 13, wherein the mounting apparatus is operable to mount a hose having a high-voltage line from the stationary part of the C-arch X-ray system to an X-ray emitter on the C-arm.

* * * * *